(12) United States Patent
Kawasaki et al.

(10) Patent No.: US 7,228,166 B1
(45) Date of Patent: Jun. 5, 2007

(54) BIOLOGICAL LIGHT MEASURING INSTRUMENT

(75) Inventors: Shingo Kawasaki, Abiko (JP); Noriyoshi Ichikawa, Ibaraki (JP); Fumio Kawaguchi, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 1118 days.

(21) Appl. No.: 10/049,313

(22) PCT Filed: Sep. 13, 2000

(86) PCT No.: PCT/JP00/06282

§ 371 (c)(1), (2), (4) Date: Feb. 12, 2002

(87) PCT Pub. No.: WO01/19252

PCT Pub. Date: Mar. 22, 2001

(30) Foreign Application Priority Data

Sep. 14, 1999 (JP) ............................. 11-260453
Jan. 20, 2000 (JP) ............................. 2000-011641

(51) Int. Cl.
*A61B 6/00* (2006.01)

(52) U.S. Cl. .................. 600/476; 600/473; 600/424

(58) Field of Classification Search ............. 600/473, 600/476; 382/142, 133
See application file for complete search history.

(56) References Cited

U.S. PATENT DOCUMENTS

| 4,417,591 A | * | 11/1983 | Culver ................. 600/544 |
| 5,215,095 A | * | 6/1993 | Macvicar et al. ........ 600/425 |
| 5,438,989 A | | 8/1995 | Hochman et al. |
| 5,465,718 A | | 11/1995 | Hochman et al. |
| 6,196,226 B1 | | 3/2001 | Hochman et al. |
| 6,233,480 B1 | | 5/2001 | Hochman et al. |
| 6,591,130 B2 | * | 7/2003 | Shahidi ................. 600/424 |

FOREIGN PATENT DOCUMENTS

| JP | A-9-19408 | 1/1997 |
| JP | A-9-98972 | 4/1997 |
| JP | A-9-149903 | 6/1997 |

OTHER PUBLICATIONS

MEDIX vol. 30, Eiju Watanabe.
Journal of Neurosurgery, vol. 76, pp. 315-318, 1992.
1995 and Medical Physics, vol. 22, pp. 1997-2005.
Up-to-date Medical Treatment, vol. 5, No. 2, pp. 76-78, 1998.

* cited by examiner

*Primary Examiner*—Brian L. Casler
*Assistant Examiner*—John F Ramirez
(74) *Attorney, Agent, or Firm*—Antonelli, Terry, Stout & Kraus, LLP.

(57) ABSTRACT

A biological light measuring instrument for illuminating a subject with a plurality of beams of light from a plurality of illuminating positions, measuring the light beams transmitted through the subject, and creating a topographic image showing ecological information about the inside of the subject, comprising unit for creating three-dimensional coordinate data representing the relationship among the illuminating positions and a reference point on the subject and the relationship between the light measuring position and the reference point, unit for setting the illuminating positions and light measuring position on a three-dimensional shape image of the subject according to the three-dimensional coordinate data, and unit for creating a three-dimensional topographic image according to the three-dimensional coordinate data, and unit for superposing the three-dimensional topographic image on the shape image while maintaining the relationships of the illuminating positions and the light measuring position.

25 Claims, 11 Drawing Sheets

BIOLOGICAL LIGHT MEASURING INSTRUMENT

TECHNICAL FIELD

The present invention relates to biological light measuring instruments for measuring information such as circulation of the blood and a change in hemoglobin inside an organism by using light beams and more particularly, to a biological light measuring instrument having the function of displaying an image synthesized with a morphological image.

BACKGROUND ART

As an instrument capable of measuring the circulation of blood/blood circulation movement and a change in hemoglobin inside an organism easily and noninvasively, an instrument has been proposed which measures the inside of an organism by irradiating light beams of wavelengths ranging from visible rays to infrared rays to the organism and detecting light reflected from the organism (for example, JP-A-9-98972 and JP-A-9-149903).

The biological light measuring instrument is applied to clinics and in case the head, for instance, is a subject to be measured, an activated state of hemoglobin change inside a brain and a local internal bleeding inside the brain can be measured and besides, motion, feeling and the highly-graded cerebral function representing thinking that are related to a change in hemoglobin inside the brain can be measured. For example, Eiju Watanabe (MEDIX VOL30) reports that a change in local cerebral blood flow (epileptic focus) during an epileptic fit can be captured by means of a light measuring instrument (optical topography instrument).

In the conventional light measuring instrument, however, a local change in hemoglobin inside the brain is displayed on a two-dimensional plane representative of an arrangement of light irradiators and photodetectors, so that the three-dimensional positional relation between the light irradiator and photodetector and the subject head is not clarified, making it difficult to specify which region of the brain the hemoglobin change occurs in. Accordingly, even in the case of the aforementioned application of measurement results of the epileptic focus to clinics, for instance, a brain site to be cut off through a surgical operation is difficult to specify.

DISCLOSURE OF INVENTION

Accordingly, it is an object of the present invention to provide a light measuring instrument in which mount positions of light irradiators and photodetectors during light measurement of a subject are clarified three-dimensionally and information obtained through the light measurement can be imaged in an accurate positional relationship either on a three-dimensional morphological image such as a MR or CT or on a wire frame image that depicts an external form of a measuring subject with contours of the subject and a plurality of ellipses.

According to the present invention, a biological light measuring instrument for attaining the above object comprises light irradiation means for irradiating light beams to a subject from a plurality of light irradiation positions (irradiation positions), a plurality of light detection means for detecting light beams irradiated from the plurality of light irradiation positions and passing through the inside of the subject at a plurality of detection positions (condensing positions) arranged near the plurality of light irradiation positions, and signal processing means for preparing a topographic image representative of biological information about the inside of the subject by using quantities of light detected by the light detection means at individual detection positions, wherein the signal processing means includes means for inputting morphological image data of the subject prepared by a separate image diagnostic device, means for inputting position information indicative of positional relationships between the light irradiation and light detection positions and reference points provided on the subject, and means for arranging the light irradiation positions and light detection positions on the morphological image data on the basis of the position information and arranging and displaying a three-dimensional topographic image prepared on the basis of the coordinate data on the three-dimensional morphological image.

Also, the signal processing means also arranges the topographic image inside the subject at a predetermined depth from the subject surface in the three-dimensional morphological image.

The signal processing means further includes means for preparing a three-dimensional wire frame image of the subject, plotting thereon the irradiation positions and detection positions and displaying a three-dimensional topographic image on a resulting image in a superposed fashion.

In the biological light measuring instrument of the present invention, the morphological image data is measured in advance with, for example, an X-ray CT device or MRI device and at least one reference point is preferably set on the subject during the measurement to include data of the reference point. The position information is three-dimensional coordinate data measured by a three-dimensional position device of mechanical or magnetic gradient type, for instance and includes the positional information of the light irradiation positions, light detection positions and reference points.

By making the reference points on the morphological image coincident with coordinate data of the reference points, the signal processing means can arrange the light irradiation positions and light detection positions on the morphological image data and arrange the topographic image on the morphological image data.

With the biological light measuring instrument constructed as above, a site where a local blood flow or a hemoglobin change takes place can be confirmed on the morphological image. Accordingly, during an epileptic operation for instance, only a focus site can be removed accurately while confirming, on the morphological image, the focus site at which the local hemoglobin change occurs. This can suppress damage to a brain to a minimum and avoid a danger of unnecessarily heavy physical function anesthetization.

Further, by arranging the topographic image inside the subject at a predetermined depth from the subject surface when the topographic image is arranged on the morphological image, the position of a site undergoing light measurement, for example, a position on the brain surface can be displayed accurately.

BEST MODE FOR CARRYING OUT THE INVENTION

Embodiments of a biological light measuring instrument of the invention will be described in greater detail with reference to the drawings.

Figure 1:
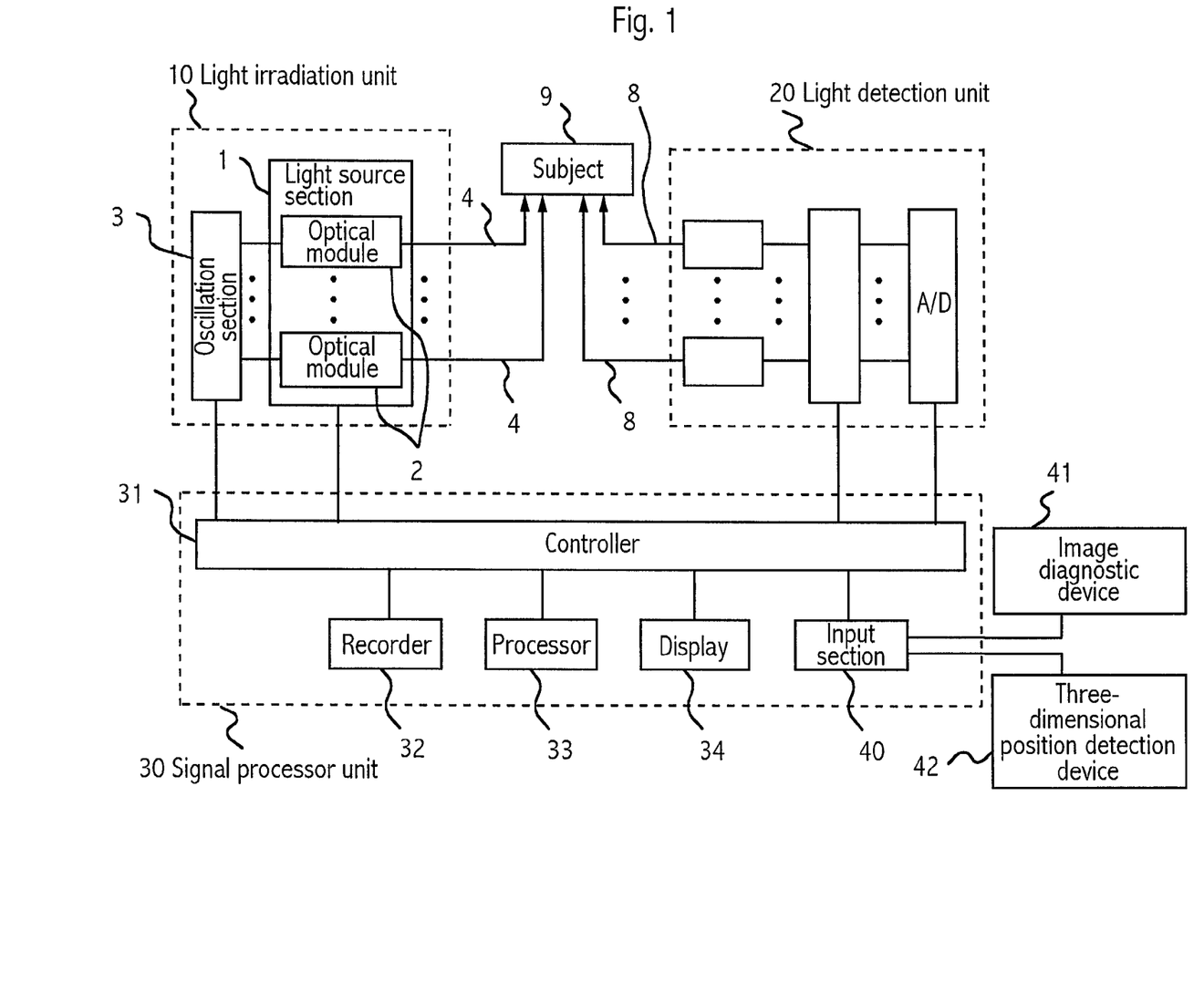
FIG. 1 is a block diagram showing an embodiment of a biological light measuring instrument of the invention.

FIG. 1 is a construction diagram showing one embodiment of the biological light measuring instrument of the invention and the light measuring instrument comprises a light irradiation unit 10 for irradiating beams of light mainly to a subject 9, a light detection unit 20 for detecting light beams transmitting through the subject 9, and a signal processing unit 30 for controlling drive of the light irradiation unit 10 and light detection unit 20 and preparing a topographic image representative of biological information of the subject 9 on the basis of quantities of light detected by the light detection unit 20.

The light irradiation unit 10 includes a light source section 1 comprised of a plurality of optical modules 2, an oscillation section 3 for modulating light beams luminescing from the optical modules 2 and optical fibers 4 connected to the respective optical modules 2. In the present embodiment, an instance where the light source section 1 has four optical modules 2 and each optical module luminesces light beams of two kinds of different wavelengths will be described but the number of optical modules and the kind (number) of light beams luminescing therefrom are not limited to the above.

Figure 2:
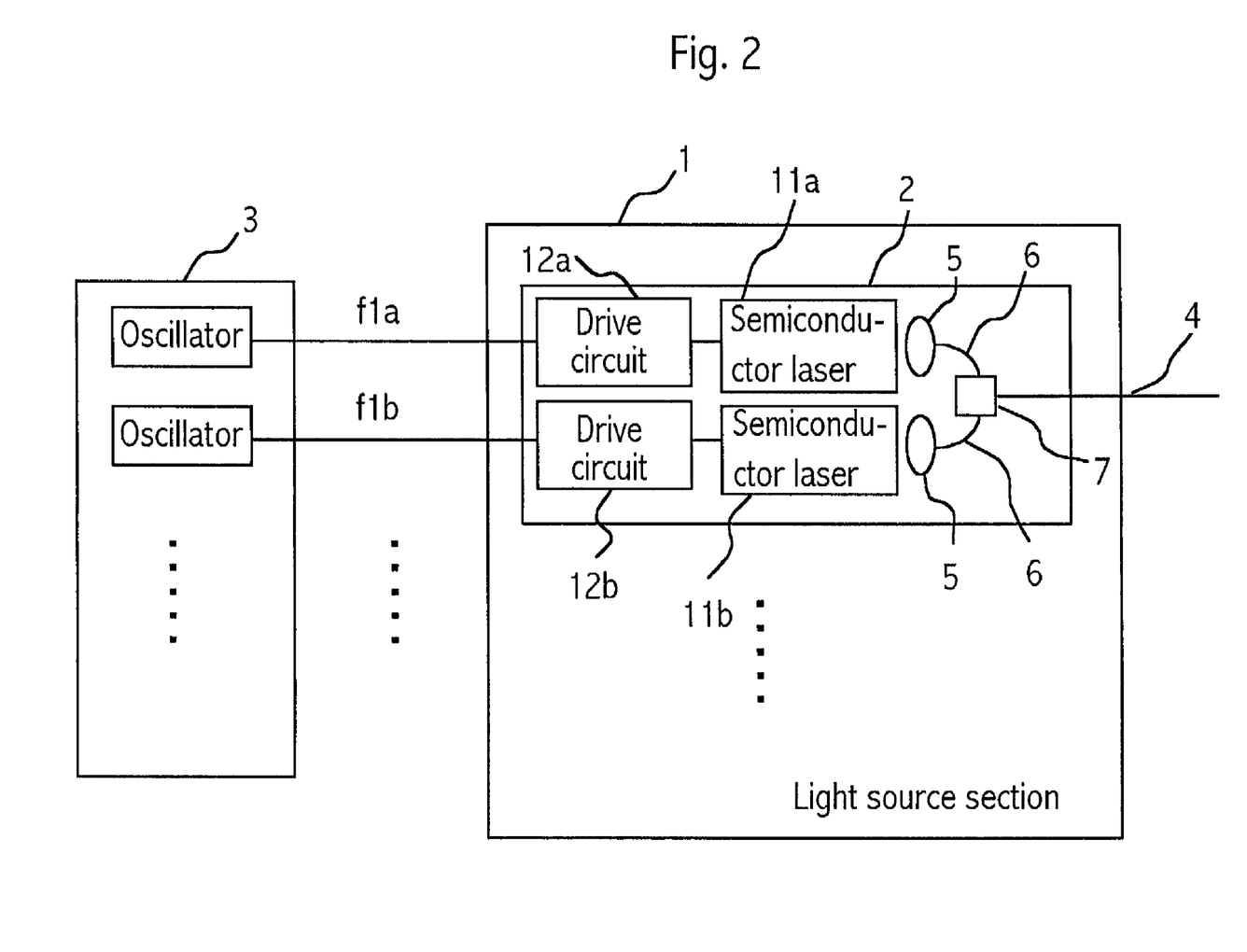
FIG. 2 is a diagram showing details of a light irradiation unit of the FIG. 1 biological light measuring instrument.

Details of the light source section 1 are shown in FIG. 2. As shown, each of the optical modules 2 has two semiconductor lasers 11a and 11b and drive circuits 12a and 12b for the semiconductor lasers 11a and 11b. The semiconductor lasers 11a and 11b irradiate light beams of different wavelengths ranging from visible rays to infrared rays. The wavelengths differ depending on a subject to be measured but for example, in the case of measurement of a change in hemoglobin, light beams of two wavelengths of 780 nm that is easily absorbable by a red blood corpuscle having oxygen and 830 nm that is easily absorbable by a red blood corpuscle having oxygen are irradiated. It is to be noted that the light source section 1 may use a light emitting diode in place of the semiconductor laser.

The oscillation section 3 has 8 oscillators of different oscillation frequencies in conformity with the number of semiconductor lasers in the optical modules 2.

The semiconductor laser drive circuits 12a and 12b apply DC bias current to the semiconductor lasers 11a and 11b while applying thereto different frequencies f1a and f1b from the oscillators, thereby modulating light beams emitted from the semiconductor lasers 11a and 11b. For the modulation, either analog modulation based on sine waves or digital modulation based on rectangular waves having different time intervals, respectively, may be used.

The light beams emitted from the semiconductor lasers 11a and 11b are admitted to optical fibers 6 by means of condensing lenses 5 connected to the semiconductor lasers 11a and 11b, respectively. The light beams of two wavelengths admitted to the respective optical fibers 6 are guided, optical module by optical module, to a single optical fiber, that is, an optical fiber 4 for irradiation through an optical fiber coupler 7.

The other end of the irradiation optical fiber 4 having one end connected to the optical fiber coupler 7 is fixed, together with an optical fiber 8 for detection of the detection unit 20 to be described later, to a fitting member not shown so as to be brought into a predetermined arrangement and is then mounted to the subject. End surfaces of these optical fibers come into soft contact with the surface of the subject so that the light beams from the other ends of the irradiation optical fibers 4 may be irradiated by way of 4 irradiation positions on the surface of the subject 9 and light rays reflected from the subject may be detected by detection optical fibers 8 arranged at 5 detection positions on the surface of the subject. The ends of the optical fibers mounted to the fitting member are called a probe. The fitting member for mounting the optical fibers to the subject can be shaped variously to take the form of a belt or helmet in accordance with the subject to be examined and for example, a known fitting member in the biological light measuring instrument described in JP-A-9-149903 may be used.

Figure 3:
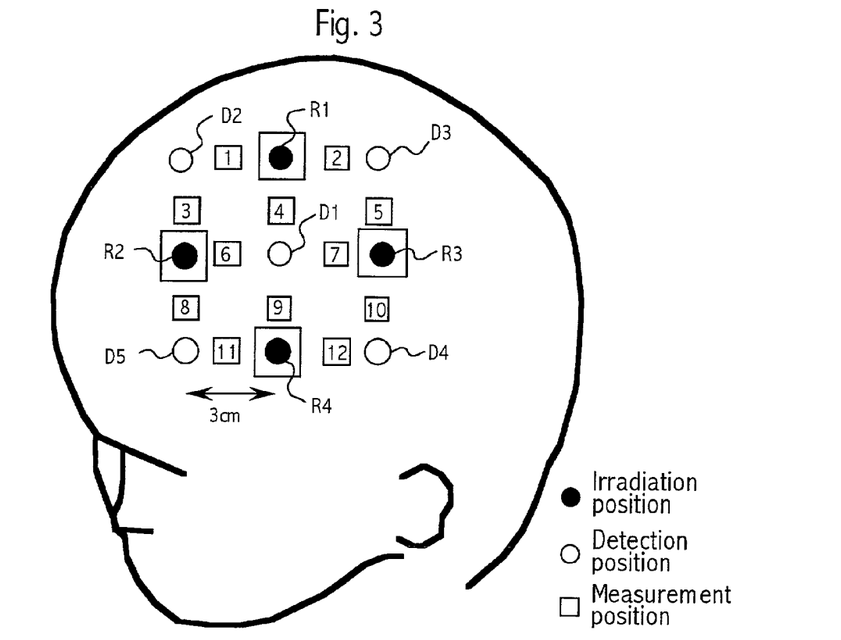
FIG. 3 is a diagram showing an embodiment of the arrangement of light irradiation positions and detection positions.

FIG. 3 shows an example of the arrangement of irradiation positions and detection positions. In the illustrated example, 4 irradiation positions R1 to R4 are shown corresponding to the 4 irradiation optical fibers 4 and these irradiation positions R1 to R4 are arranged alternately with detection positions D1 to D5 on a square lattice. Then, on the assumption that a measurement position is at the middle point between adjacent irradiation position and detection position, 12 combinations of adjacent irradiation and detection positions exist and the number of measurement positions, that is, of measurement channels amounts up to 12.

The pitch between the adjacent irradiation and detection positions is not particularly limited and can be changed suitably in accordance with the measuring site, for instance. It is reported that with the pitch set to 3 cm, light beams detected at the individual detection positions have passed through skin and skull to have information about a cerebrum (for example, "Intracerebral penetration of infrared light" by P. W. McCormic et al, Journal of Neurosurgery, Vol. 76, pp. 315–318, 1992). Accordingly, by setting the 12 measurement channels in the aforementioned irradiation/detection position arrangement, measurement at a 6 cm×6 cm area throughout the cerebrum can be assured.

Figure 4:
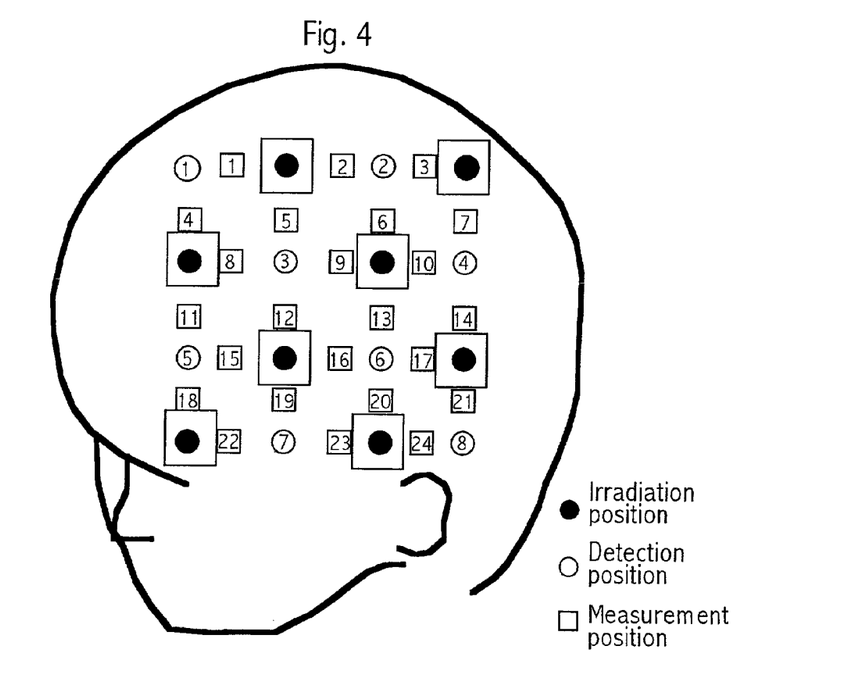
FIG. 4 is a diagram showing another embodiment of the arrangement of light irradiation positions and detection positions.
Figure 5:
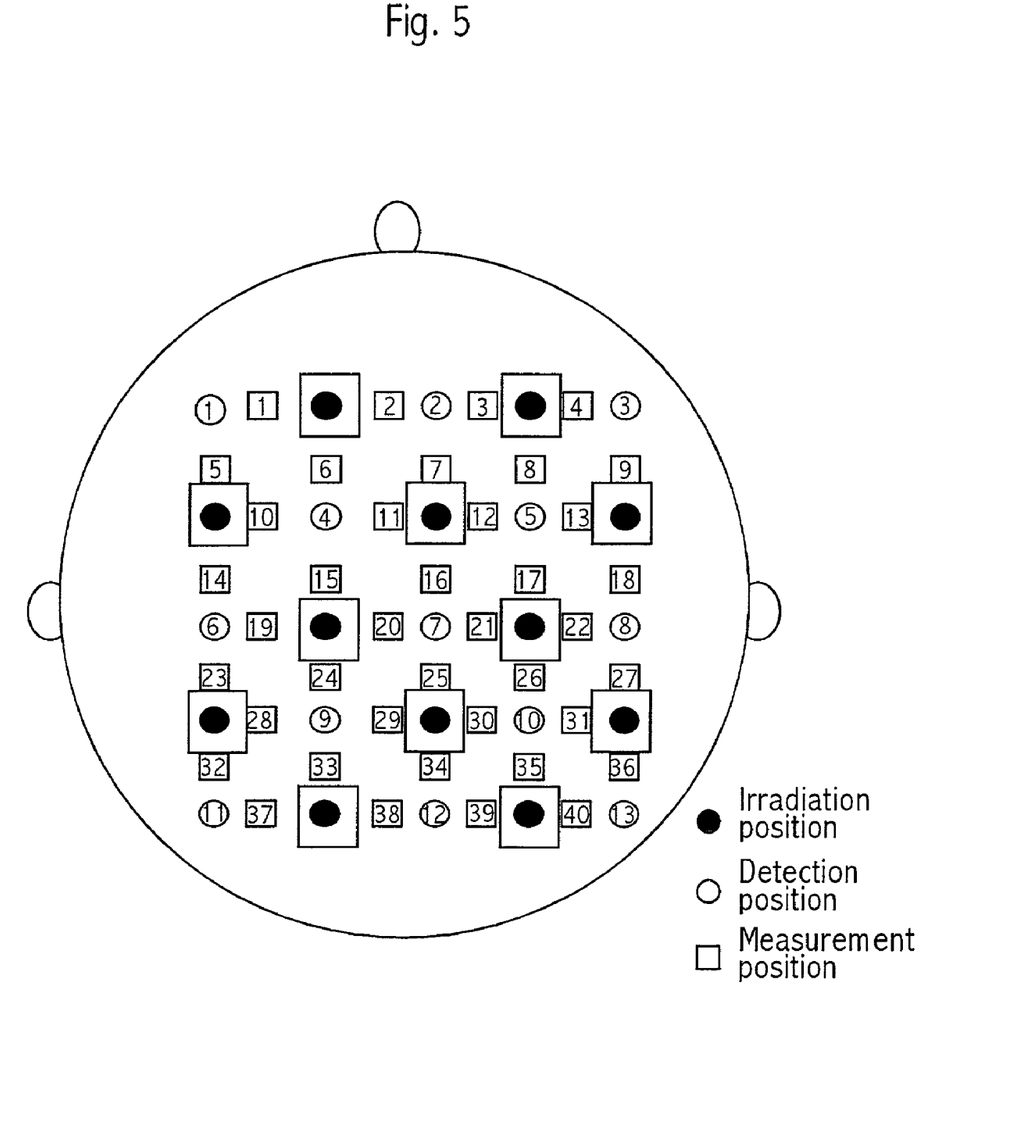
FIG. 5 is a diagram showing still another embodiment of the arrangement of 4 light irradiation positions and detection positions.

In the illustrated embodiment, an instance where the number of measurement channels is 12 for simplicity of explanation but by further increasing the number of light irradiation positions and light detection positions arranged in a lattice form, the measurement channels can be further increased to expand the measuring area. As other embodiments, a light irradiation/detection arrangement in 24-channel measurement is shown in FIG. 4 and that in 40 channels is shown in FIG. 5.

Figure 6:
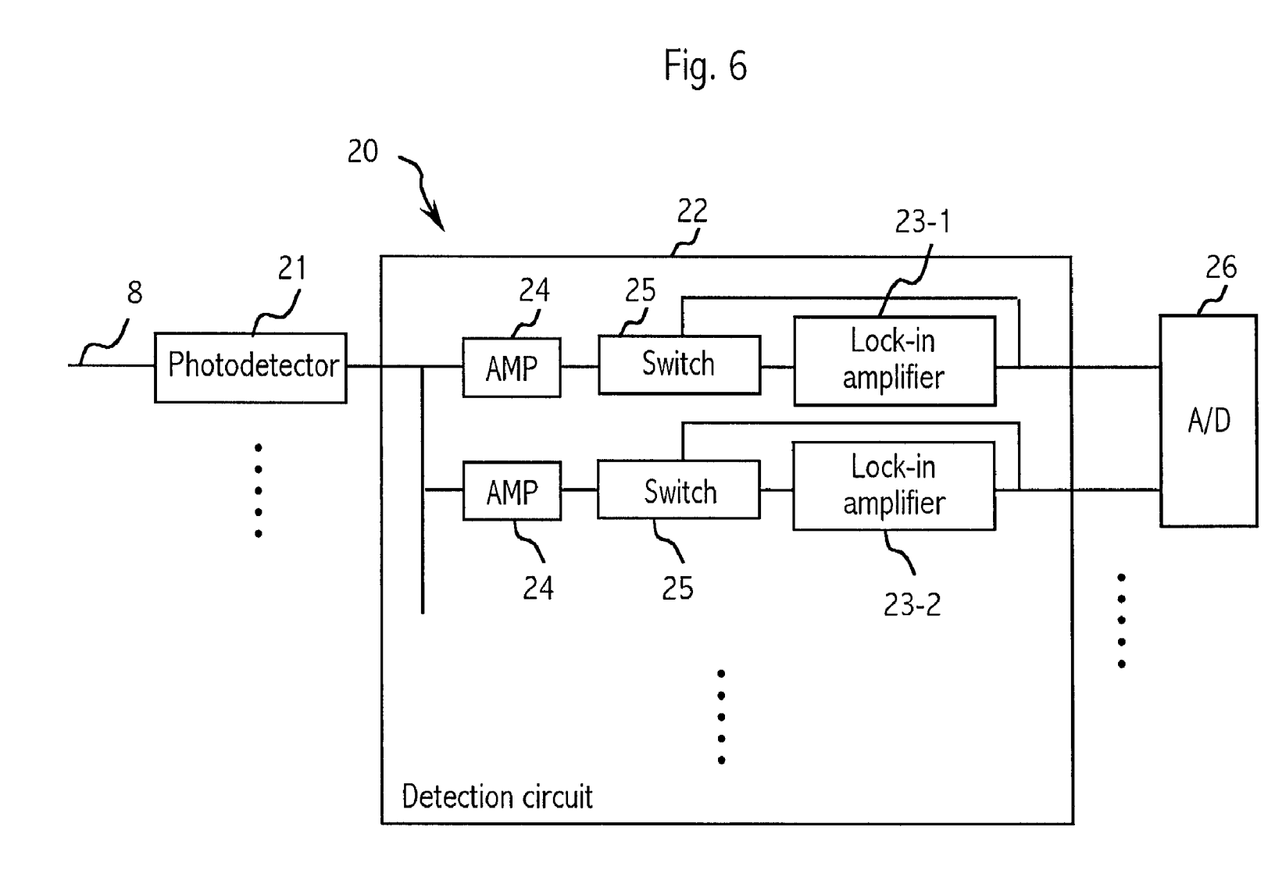
FIG. 6 is a diagram showing details of a light detection unit of the FIG. 1 biological light measuring instrument.

FIG. 6 is a diagram showing details of the detection unit 20. The detection unit 20 includes photodetectors 21 and detection circuits 22. In the drawing, only a detection unit to which one of a plurality of (here, five) detection optical fibers 8 corresponding to the individual detection positions is connected is shown but the plurality of (here, five) detection optical fibers 8 corresponding to the respective detection positions are respectively connected with the detection unit 20 including photodetector 21 and the detection circuit 22 as well as A/D converters 26.

Each photodetector 21 is adapted to convert a light signal into an electric signal in order that a light beam incident on a detection optical fiber can be converted into an electric signal proportional to a quantity of the light beam and the electric signal can be sent to the detection circuit 22. As the photodetector 21 as above, a photodiode or photomultiplier tube, for instance, can be used. Especially, an avalanche photodiode capable of realizing high-sensitivity light measurement is preferable.

The detection circuit 22 is comprised of a lock-in amplifier module having circuits for selectively detecting modulation signals, for example, a plurality of lock-in amplifiers 23-1, 23-2 . . . , amplifiers 24 and switches 25 and is operative to selectively detect modulated signals corresponding to an irradiation position and the wavelengths. For example, in the case of a detection circuit associated with detection position D1 of FIG. 3, with the aim of detecting 8 signals of modulation frequencies f1$a$, f1$b$, f2$a$, f2$b$, f3$a$, f3$b$, f4$a$ and f4$b$ corresponding to light beams of two wavelengths respectively irradiated from irradiation positions R1 to R4 adjacent to the detection position D1, there are provided 8 lock-in amplifiers 23-1 to 23-8 using the modulation frequencies as reference signals. The lock-in amplifier 23-1 uses a reference signal of modulation frequency f1$a$ to selectively detect a light beam of 780 nm wavelength and f1$a$ modulation frequency irradiated from the irradiation position R1. Similarly, the lock-in amplifier 23-2 uses a reference signal of modulation frequency f1$b$ to selectively detect a light beam of 830 nm wavelength and modulation frequency f1$b$ irradiated from the irradiation position R1. Through this, for a measurement position between the detection position D1 and the irradiation position R1, two signals corresponding to the light beams of two wavelengths can be picked up. For a measurement position between the detection position D1 and each of the irradiation positions R2 to R4, two signals can be picked up similarly from each of the lock-in amplifiers 23-3 to 23-8.

In the case of each of the detection positions D2 to D5, there are only two adjoining irradiation positions and so, the number of lock-in amplifiers 23 may be 4 in accord with two wavelengths and for respective two measurement positions between one detection position and two irradiation positions, two signals are picked up by means of 4 lock-in amplifiers. Accordingly, in the case of the irradiation/detection position arrangement shown in FIG. 3, for the respective 12 measurement positions, signals of two channels can be picked up by means of 24 lock-in amplifiers in total.

Outputs of the lock-in amplifiers 23-1, 23-2, . . . are respectively converted into digital signals by means of the analog/digital converters 26 and then sent to the signal processing unit 30. In the present embodiment, the lock-in amplifier is shown as the modulated signal detection circuit corresponding to the case of analog modulation but in case the digital modulation is used, a digital filter or digital signal processor may be used for modulated signal detection.

The signal processing unit 30 includes, as shown in FIG. 1, a controller 31 for controlling the aforementioned light irradiation unit 10 and light detection unit 20, a recorder 32 for recording signals measured by the light detection unit 20 and results of calculation of the signals, a processor 33 for calculating digitally converted measured signals to prepare a topographic image by using, for example, a calibration curve of hemoglobin precedently stored and a display 34 for displaying the topographic image and the like. It further includes an input section 40 for inputting data from an image diagnostic device 41 such as a MRI or X-ray CT device and a three-dimensional position detection device 42. Three-dimensional morphological image data from the image diagnostic device 41 and three-dimensional coordinate data from the three-dimensional position detection device 42 are transferred directly or via a recording medium to the input section 40.

The techniques for calculating a change in oxidized hemoglobin concentration, a change in deoxidized hemoglobin concentration and besides a change in total hemoglobin concentration indicative of the total of the above hemoglobin concentration, these changes being due to brain activities, by using quantities of light beams of two wavelengths at the individual measurement positions and displaying the calculated change in the form of a topographic image on the display are described in, for example, JP-A-9-19408, "Spatial and temporal analysis of human motor activity using noninvasive NIR topography" by Atushi Maki et al, 1995 and Medical Physics, Vol. 22, pp. 1997–2005. In the present invention, too, these methods can be employed for calculation of measured signals.

The morphological image data is obtained by photographing the same subject with the image diagnostic device 41 such as a MRI or X-ray CT device in advance of measurement based on the biological light measuring instrument of the invention and includes data of specified reference points set on the subject, preferably, three or more reference points. Such reference points can be set by photographing the subject while sticking predetermined reference point markers on the subject. As the reference point marker, a small piece made of X-ray absorbable material such as a metal ball or metal foil, for instance, may be used for CT and a capsule filled with a substance exhibiting behavior different from that of a nuclide to be measured (typically, hydrogen) in nuclear magnetic resonance, for example, a fat soluble medicine can be used for MRI. By incorporating the reference points into the image data in this manner, position matching of the image data to the three-dimensional coordinate data to be described later can be ensured, thus making it possible to arrange the topographic image obtained in the biological light measurement on the morphological image. The position at which the reference point marker is applied is not particularly specified but the reference marker is applied near a measuring site of the subject and in the case of brain measurement for instance, the reference marker is stuck on three points of left ear position, right ear position and nose recess position (nasion).

In another embodiment for incorporating the reference points into the image data, reference points such as for example nose position and left and right ear positions may be designated on inputted image data manually afterwards.

The three-dimensional position detection device 42 detects positions of the individual probes (light irradiation positions and light detection position) and positions on which the reference point markers are stuck, under the condition that the subject is mounted with fitting members of the biological light measuring instrument (the fitting member to which the light irradiation fiber and light detection fiber are fixed) and applied with the aforementioned reference point markers, and delivers them as three-dimensional coordinate data. As the three-dimensional position detection device 42, there are available mechanical, magnetic gradient and optical types and any type can be adopted.

When the reference points are measured with the magnetic gradient type, a magnetic generation device is placed behind the subject and information about a distance from this location is inputted as position information.

An input device is applied to the individual reference points and the probes to input position information of the respective points and X, Y and Z coordinate axes information and angular information of a pen type input device are inputted.

As the three-dimensional position detection device, a position detection means termed a neuronavigator described in "The present condition and future of neuronavigator" by Hidehisa Watanabe, Up-to-date Medical Treatment, Vol. 5, No. 2, pp. 76–78, 1998 can be used.

The processor 33 inputs the morphological image data and coordinate data and enlarges or contracts coordinate values of the light irradiation and light detection positions in order that reference points on the morphological image data coincide with coordinate data corresponding to the reference points.

Figure 7:
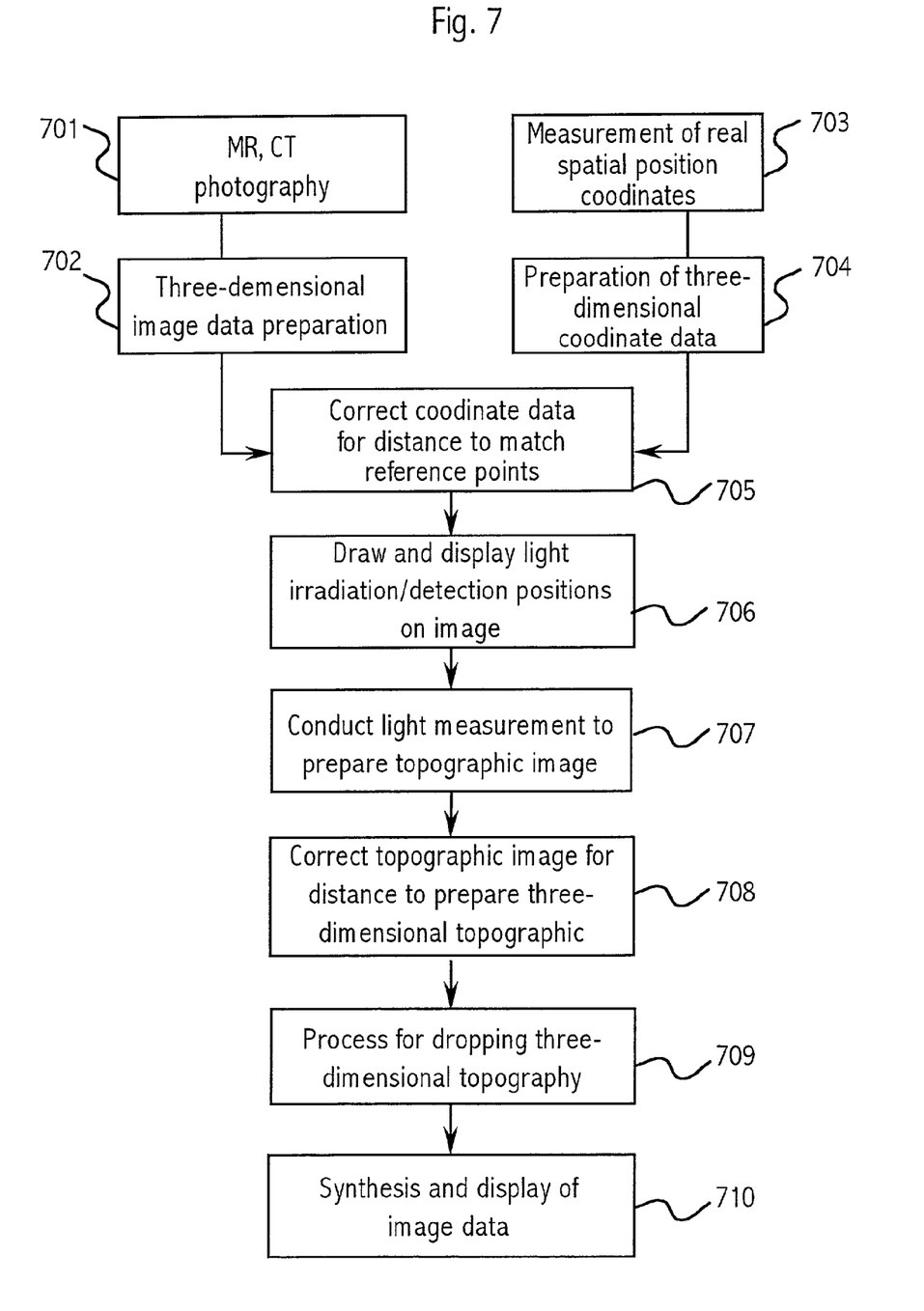
FIG. 7 is a flow chart showing an embodiment of processing in the biological light measuring instrument of the invention.

Next, an embodiment of biological light measurement using the biological light measuring instrument constructed as above will be described with reference to FIG. 7. In this embodiment, an instance will be described in which a head is a site to be measured and a change in hemoglobin in the brain surface is measured to prepare a three-dimensional topographic image.

Before conducting the biological light measurement, a three-dimensional image of a subject is prepared by means of the MR or CT device. At that time, the subject is applied with reference point markers at 3 points near the measuring site and then is photographed (steps 701 and 702). The prepared three-dimensional image data is transferred from the input section 40 to the recorder 32 of signal processing unit 30.

Subsequently, fitting members for biological light measurement are mounted to the head of the subject applied with the reference point markers and real spatial coordinates of positions of the reference points, light irradiation positions and light detection positions are measured by means of the three-dimensional position detection device (steps 703 and 704). Three-dimensional coordinate data measured by the three-dimensional position detection device is transferred from the input section 40 to the recorder 32 of signal processing unit 30.

The processor 33 brings the real spatial coordinate values of the reference points measured with the three-dimensional position detection device into matching to the reference points on the three-dimensional image by performing enlargement, contraction and distance correction (705). Thereafter, the light irradiation positions and light detection positions are corrected for distance on the real spatial coordinates on the basis of distance correction factors of the matched reference points and then are drawn on the image data (706).

Figure 8A:
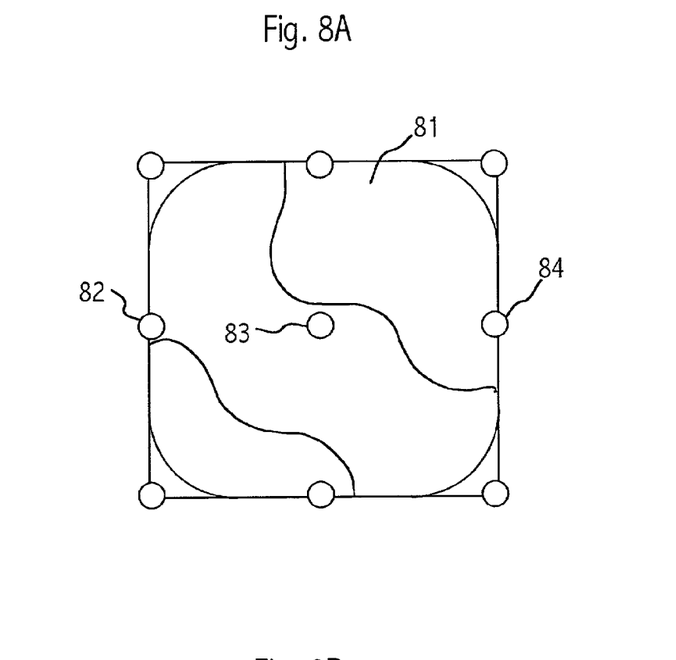
FIGS. 8A and 8B are diagrams for explaining a topographic image prepared in the FIG. 7 process and an image process.

Under this condition, the biological light measurement of the subject is started (707). Namely, light beams of two wavelengths respectively modulated with predetermined modulation frequencies are irradiated from the light irradiation positions and light beams transmitting through the subject are detected at adjacent detection positions. Through this, for each measurement position between the light irradiation position and light detection position, a signal corresponding to a quantity of transmitting light beam can be obtained. The signal processing unit 30 determines a change in hemoglobin at each measurement position from the thus obtained quantity of light by using the hemoglobin calibration curve recorded in advance and prepares equi-quantity curves (a graph depicted by connecting points of equal quantity with lines) as shown in FIG. 8A or a graduation display or color tone display. An image in which the equi-quantity curves or the graduation display (color tone display) is drawn on a plane on which the measurement positions are arranged two-dimensionally is a topographic image 81 and this image is similar to that created in the conventional biological light measurement. In FIG. 8A, 82 and 84 designate light irradiation positions and 83 designates a light detection position.

Subsequently, the signal processing unit 30 corrects the two-dimensional topographic image for distance to convert the two-dimensional topographic image into a three-dimensional topographic image. The distance correction is a process in which when the distance is large and so the signal level of the two-dimensional topographic image is low, a large value of weight D is multiplied to increase the signal and when the distance is small and so the signal level is high, a small value of weight D is multiplied to decrease the signal, and through this process, an accurate topographic image corrected for distance can be prepared. Two-dimensional topographic image data Hb referred to herein is calculated and displayed on the assumption that the distance between the light irradiation position and light detection position has a constant value c (for example, 30 mm) and therefore, in this process, an accurate distance d between the light irradiation position and light detection position measured with the three-dimensional position detector is used to determine new data Hb' corrected for distance pursuant to the following equation (1).

$$Hb' = Hb \times D \tag{1}$$

where D (distance) indicates D=d/c.

By matching the two-dimensional topographic image corrected for distance to the light irradiation positions and light detection positions drawn in the step 706 in this manner, a three-dimensional topographic image can be drawn (708). In this phase, spline interpolation may be made as necessary.

The three-dimensional topographic image prepared in the step 708 is contoured along the measuring surface, that is, the head surface but as has already been described, light beams detected at the individual detection positions have passed through the skin and skull to have information about the cerebrum and it is preferable that they should be displayed as brain surface information. From this viewpoint, in step 709, a process is performed in which the three-dimensional topographic image obtained in the step 708 is dropped to a predetermined depth in the normal direction of the head surface. The distance between the head surface and the brain surface may be calculated from the image data of the subject or alternatively an empirically known value can also be used.

Figure 8B:
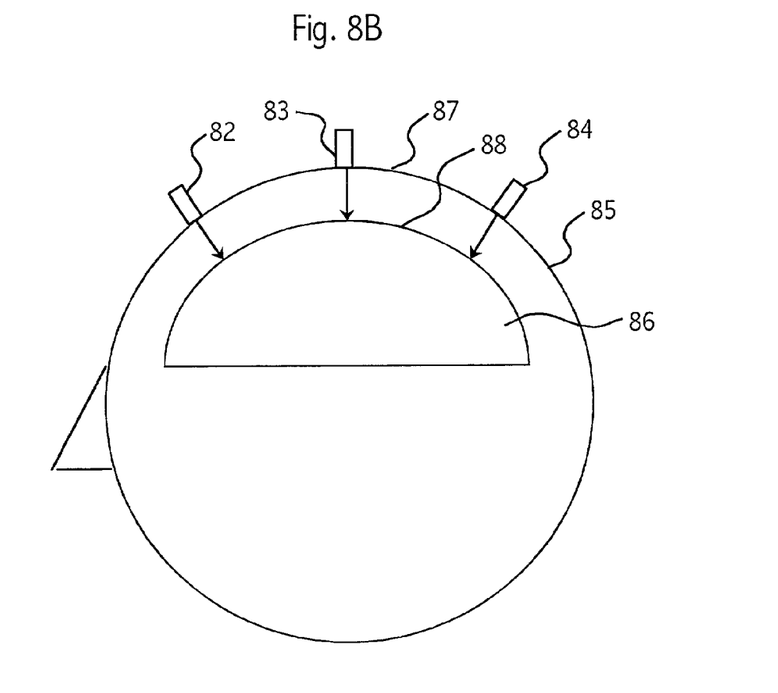

The process to be done in the step 709 is shown in FIG. 8B. FIG. 8B schematically shows a state of head 85 and brain 86 of the subject as viewed sideways. The topographic image obtained in the step 708 is drawn on head surface 87 of the subject but is moved in the normal direction as shown by arrow in the drawing, thereby drawing a topographic image on brain surface 88. In this manner, a synthesis of the three-dimensional topographic image and morphological image can be displayed (710).

Figure 9:
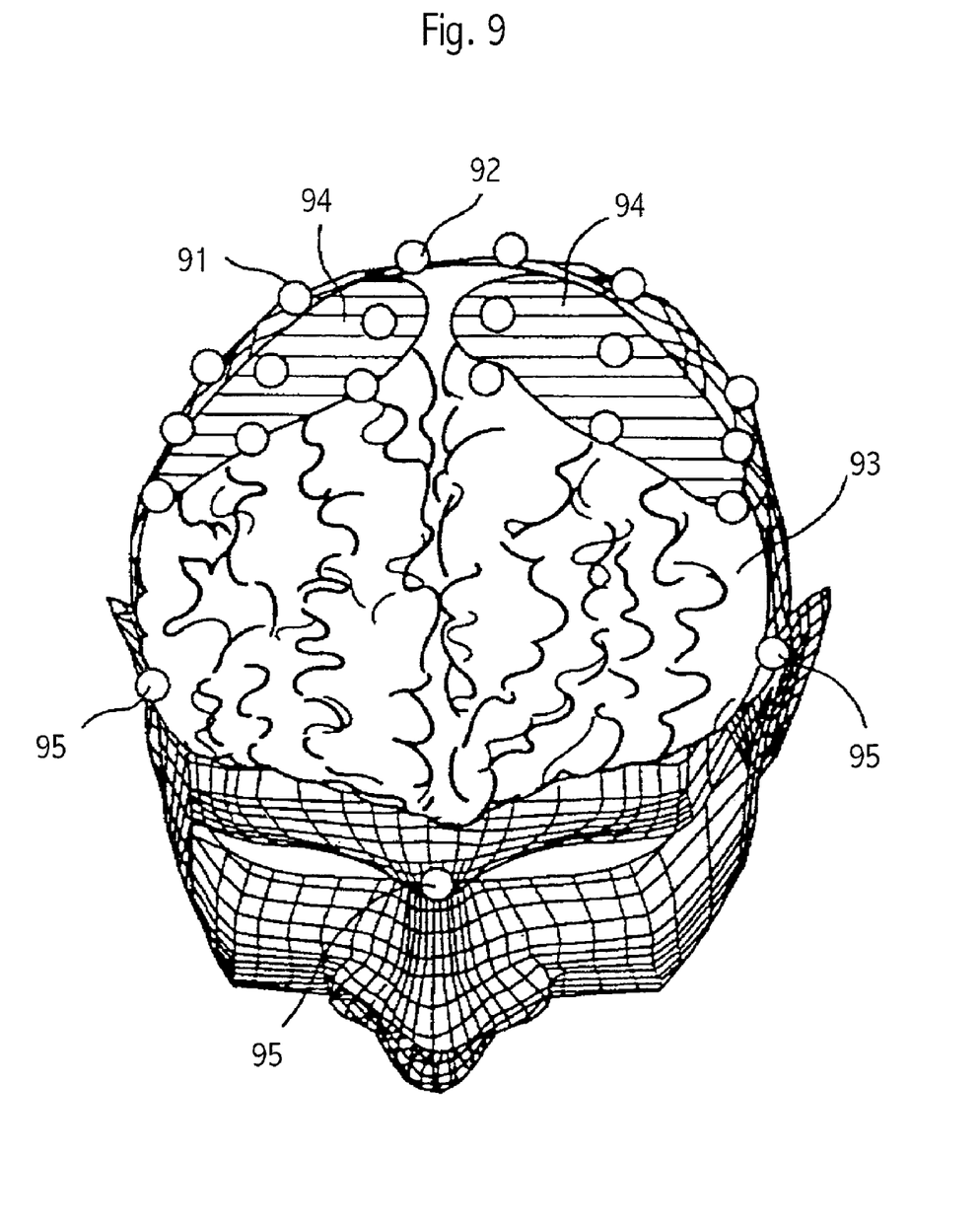
FIG. 9 is a diagram showing an example of an image displayed by the biological light measuring instrument of the invention.

An example of an image obtained through the biological light measurement as above is shown in FIG. 9. Here, a three-dimensional image of only the brain is displayed as a morphological image and the head shape is displayed in the form of a three-dimensional frame to facilitate visibility of the display but obviously the whole inclusive of the head shape may be displayed three-dimensionally.

The present embodiment is shown by way of the case where the probes in the arrangement shown in FIG. 3 are mounted to the left and right cerebrums. Light irradiation positions 91 and light detection positions 92 of the individual probes are displayed and a three-dimensional topographic image 94 obtained through the process in the step 709 is displayed at positions on brain surface 93 corresponding to the probes. In the drawing, 95 designates reference points for matching of positioning of the light irradiation positions 91 and light detection positions 92 on the image and in this example, the reference points are three of left ear position, right ear position and nose recess position (nasion).

From such an image, accurate mount positions of the individual probes (light irradiation/light detection positions) can be known and it can be known accurately which region of the brain a local change in hemoglobin occurs at.

Figure 10:
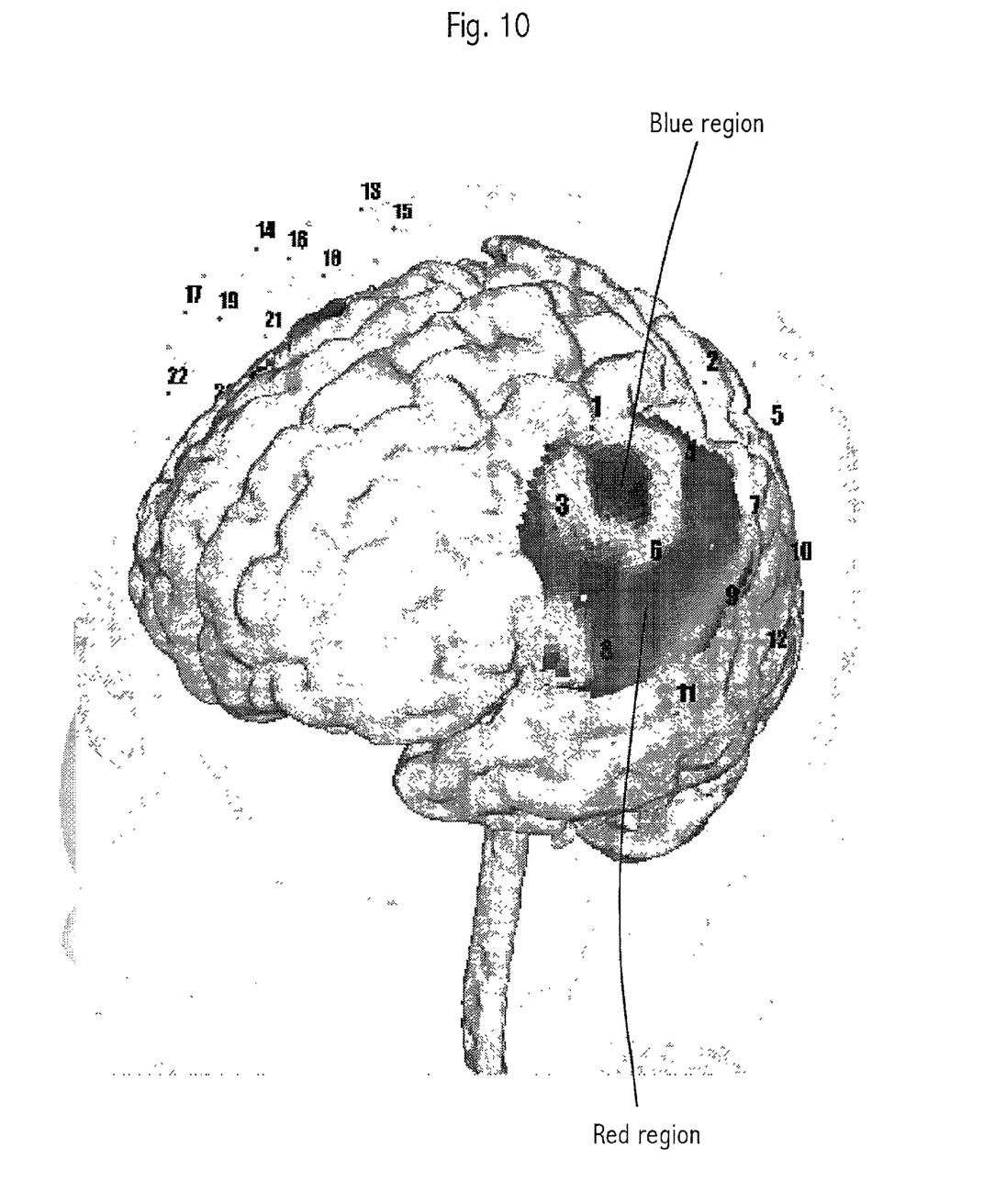
FIG. 10 is a diagram of printout of the image displayed by the biological light measuring instrument of the invention.

An actual display example is printed out as shown in FIG. 10. A topographic image is displayed on a three-dimensionally displayed brain surface in a superposed fashion. Numerical values indicate light irradiation units and detection positions.

A region where the hemoglobin concentration change level is small is displayed in blue and a region where the hemoglobin concentration change level is large is displayed in red.

Figure 11:
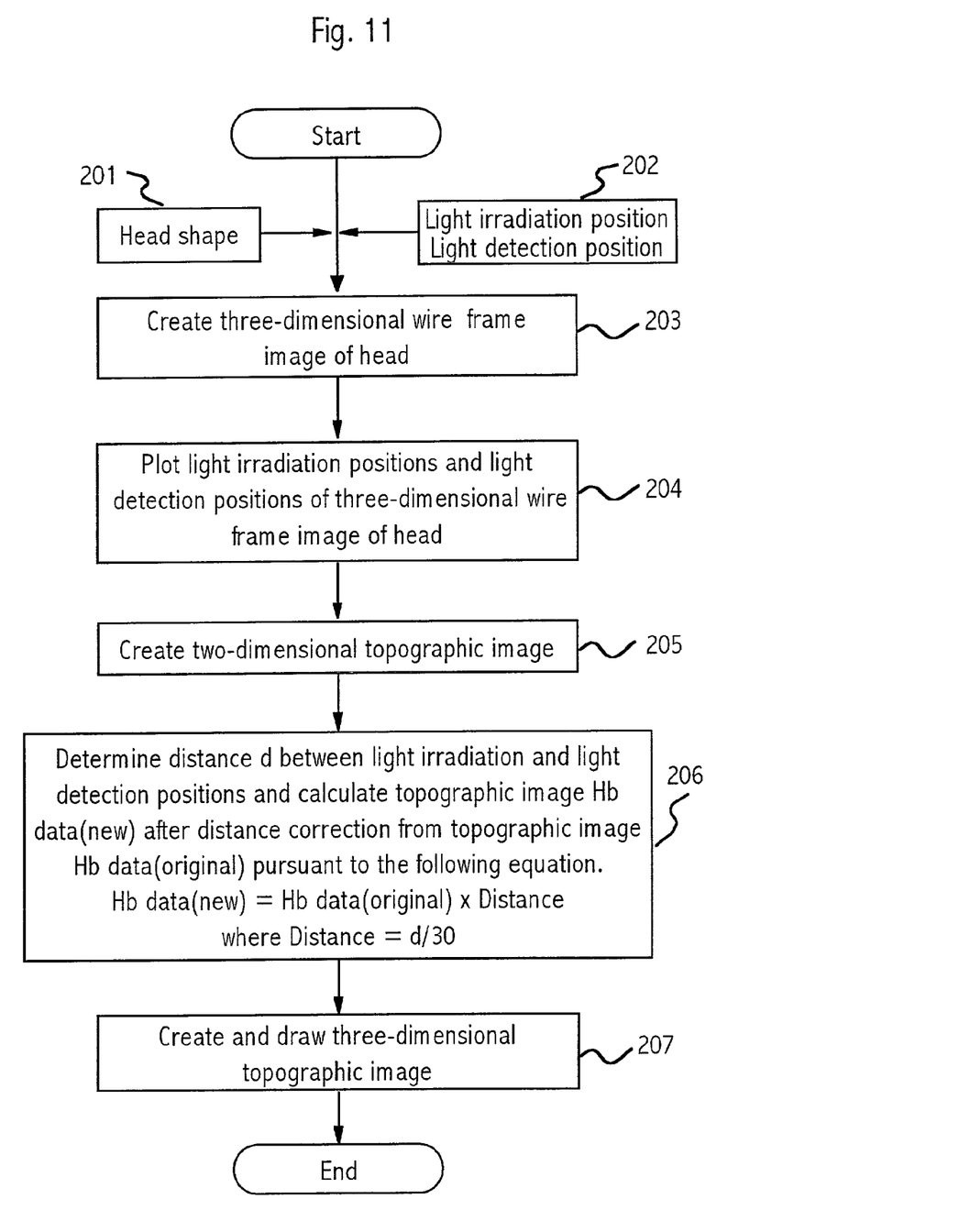
FIG. 11 is a flow chart showing another embodiment.

FIG. 11 is a flow chart of an embodiment for displaying a topographic image on a wire frame image in a superposed fashion.

Under a command for creation of a topographic image from an input means not shown, the controller 31 delivers three-dimensional position information 201 concerning a head shape and three-dimensional position information 202 concerning positions of contact between the irradiation and detection optical fibers 4 and 8 and the subject 9 from the recorder 32 to the processor 33. It is to be noted that the three-dimensional information 201 is coordinate information of all reference positions measured for the purpose of specifying an external appearance of the subject 9.

The processor 33 first creates a three-dimensional wire frame image of the head from the three-dimensional position information 201 measuring the shape of the head that is a measuring site of the subject 9. Concretely, coordinate values of four points (left ear position, right ear position, nose recess position (nasion) and occiput (inion)) measured as reference positions are used to perform parabolic approximation based on the XYZ coordinate system, thereby creating the wire frame image of the head shape.

On the basis of three-dimensional position information about light irradiation positions (irradiation positions) and light detection positions (condensing positions) that represents the three-dimensional position information 202 concerning positions of contact between the tips of irradiation and detection optical fibers 4 and 8 and the subject 9, the processor 33 creates (forms) a three-dimensional wire frame image of the head representing the measuring site (step 203).

Thereafter, the processor 33 specifies the light irradiation positions and light detection positions on the thus created three-dimensional wire frame image and plots them (step 204). Subsequently, the processor 33 carries out procedures similar to the conventional ones assuming that the distance between the light irradiation position and the light detection position is uniform amounting to a design distance of 30 mm, so as to create a two-dimensional topographic image (step 205). In the step 205, on the assumption that, for example, the light irradiation positions and the light detection positions are arranged at a pitch of 30 mm in a square lattice as shown in FIG. 3, a change in oxidized hemoglobin concentration, a change in deoxidized hemoglobin concentration and a change in total hemoglobin concentration are determined at 12 measurement positions each located midways between adjacent light irradiation position and light detection position when stimulation is applied to the brain and when stimulation is not applied to the brain. Next, a value of the change in hemoglobin concentration at each measurement position is formed into an image through, for example, three-dimensional spline interpolation and a resulting image is defined as a topographic image. Details of acquisition of the topographic image from the value of hemoglobin concentration change through the three-dimensional spline interpolation are described in JP-A-9-98972 and JP-A-9-149903 and so a detailed description will be omitted.

Then, the processor 33 calculates, for each measurement position, distance d between adjacent light irradiation position and light detection position in three-dimensional space from the read light irradiation position and light detection position 202. Since in the present embodiment the number of measurement positions is 12, the distance d between the light irradiation position and light detection position in three-dimensional space computed through the calculation amounts to 12 in number. Subsequently, on the basis of the two-dimensional light irradiation position and light detection position, the processor 33 corrects the two-dimensional topographic image Hb data (original) pursuant to equation (1) to create topographic image Hb data (new) on the basis of the three-dimensional light irradiation position and light detection position (step 206).

Next, the processor 33 converts the topographic image after correction into a topographic image along the wire frame image created in the step 203. Specifically, pixel values of individual pixels constituting the topographic image are three-dimensionally interpolated in accord with coordinates of the head wire frame image so that the topographic image may be converted into a three-dimensional topographic image.

Thereafter, the processor 33 creates a three-dimensional image in which the topographic image is superposed on the wire frame image and causes it to be displayed on the display screen of the display 34 (step 207). Accordingly, with the biological light measuring instrument of the present invention, the topographic image along the wire frame image of the subject 9 can be created.

Figure 12:
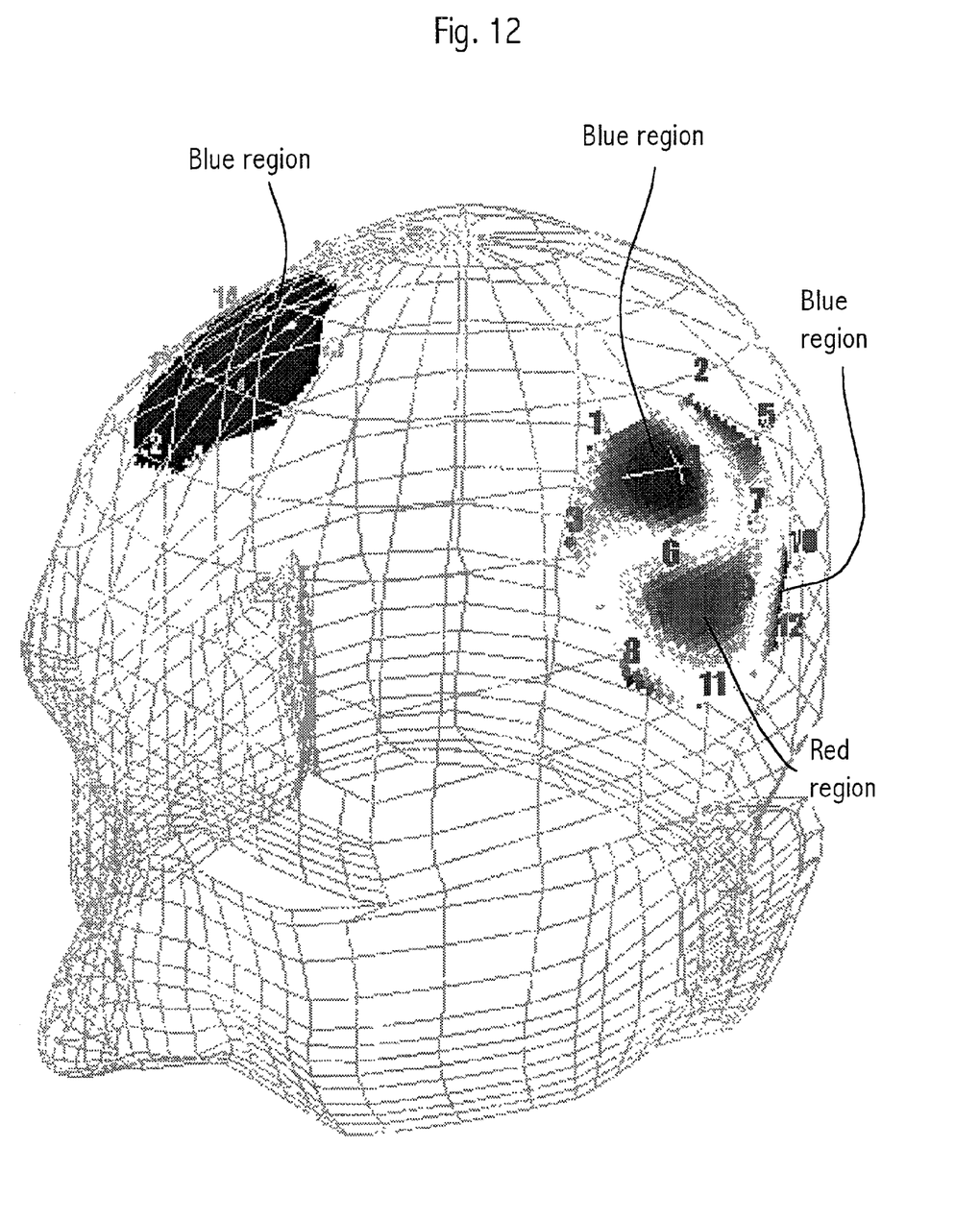
FIG. 12 is a diagram showing an example of an image displayed in another embodiment.

FIG. 12 is a diagram showing an example of the three-dimensional topographic image displayed on the wire frame image. In the present embodiment, however, a region where the level of hemoglobin concentration change due to stimulation is small is indicated in blue, a region where the concentration change level is large is indicated in red and an intermediate part is displayed in a color between blue and red.

Numerical values displayed on the wire frame image in a superposed fashion indicate channel numbers of the measurement positions, that is, the light irradiation positions and light detection positions.

As will be seen from FIG. 12, the three-dimensional topographic image representing results of the measurement and the light irradiation positions and light detection positions can be displayed on the wire frame image and hence, positions where the irradiation optical fibers and detection optical fibers contact the subject 9 can be grasped accurately. As a result, it can be grasped easily how the hemoglobin concentration changes at which position of the subject 9 and so the diagnosis efficiency can be improved.

The present embodiment is constructed such that a change in oxidized hemoglobin concentration, a change in deoxidized hemoglobin concentration and a change in total hemoglobin concentration are calculated at each measurement position at the design pitch between optical fibers during measurement and thereafter, the changes in oxidized, deoxidized and total hemoglobin concentration are corrected at the individual measurement positions with an optical fiber pitch calculated from optical fiber positions measured three-dimensionally but this is not limitative. Obviously, for example, the optical fiber pitch during measurement may first be calculated from the optical fiber positions measured three-dimensionally and on the basis of the thus calculated optical fiber pitch, the changes in oxidized and deoxidized hemoglobin concentration and the change in total hemoglobin concentration may be calculated at each measurement position.

Operation of the biological light measuring instrument of the invention has been set forth so far by way of example of light measurement of the head of the subject but the invention is in no way limited to the foregoing embodiments and can be altered variously. For example, in the flow shown in FIG. 7, the steps ranging from step 707 of light measurement to step 710 of image display may be repeated to obtain sequential images in time series. In this case, for a specified measurement site, the hemoglobin change can be displayed graphically or numerically, independently of the morphological image.

In a method for display of the morphological image, the image may be rotated about a predetermined axis or the function of enlarging a desired site may be provided. Further, the measuring subject is not limited to the head and the invention can be applied to other sites and besides to subjects other than the organism.

In the present invention, displaying the topographic image on the three-dimensional morphological image is the most effective but displaying the topographic image on the two-dimensional morphological image is also within the framework of the invention.

According to the biological light measuring instrument of the invention, the three-dimensional topographic image can be prepared and displayed on the three-dimensional image of the subject and therefore, information obtained through the biological light measurement, for example, a local change in hemoglobin can be known accurately in a relationship to a site where the change occurs.

INDUSTRIAL APPLICABILITY

By making display results according to the invention easily comparable with analytical results of other brain functions such as FMRI, PET, SPECT and the like, the diagnostic accuracy can be further improved.

The invention claimed is:

1. A biological light measuring instrument comprising:

light irradiation means for irradiating light beams from a plurality of light irradiation positions to a subject;

light detection means for detecting light beams irradiated from said plurality of light irradiation positions and passing through the inside of said subject at a plurality of detection positions arranged near said plurality of light irradiation positions;

signal processing means for preparing a topographic image representing biological information about the inside of said subject by using quantities of light detected by said light detection means at the individual detection positions; and memory means for memorizing a three-dimensional morphological image of said subject and reference points set thereon, wherein said signal processing means includes:

means for setting three-dimensional coordinate data indicative of the positional relation between said light irradiation and light detection positions and reference points set on said subject;

means for generating a three-dimensional topographic image on the basis of said three-dimensional coordinate data; and means for superimposing said three-dimensional topographic image onto said three-dimensional morphological image based on said set reference points.

2. A biological light measuring instrument according to claim 1, wherein said signal processing means further includes means for arranging said three-dimensional topographic image inside said subject at a predetermined depth from the surface of said subject in said three-dimensional morphological image.

3. A biological light measuring instrument according to claim 1, further comprising means for inputting three-dimensional morphological image data of said subject.

4. A biological light measuring instrument according to claim 1, wherein said signal processing means includes means for preparing a wire frame image of said subject as said morphological image.

5. A biological light measuring instrument according to claim 1, wherein said morphological image includes a tomographic image.

6. A biological light measuring instrument according to claim 5, wherein said morphological image includes a CT image.

7. A biological light measuring instrument according to claim 5, wherein said morphological image includes a MRI image.

8. A method of creating a topographic image in a biological light measuring instrument having means for irradiating light beams to a subject from a plurality of light irradiation positions, light detection means for detecting light beams irradiated from said plurality of light irradiation positions and passing through the inside of said subject at a plurality of detection positions near said plurality of light irradiation positions, and signal processing means for preparing a topographic image indicative of biological information about the inside of said subject by using quantities of light at individual detection positions detected by said light detection means, said method comprising the steps of:

memorizing a three-dimensional morphological image of said subject and reference points set thereon;

setting three-dimensional coordinate data indicative of the positional relation between said light irradiation and light detection positions and reference points set on said subject;

generating a three-dimensional topographic image on the basis of said three-dimensional coordinate data; and superimposing said three-dimensional topographic image onto said three-dimensional morphological image based on said set reference points.

9. A topographic image creating method according to claim 8, wherein said step of displaying includes a step of arranging said three-dimensional topographic image inside said subject at a predetermined depth from the surface of said subject in said three-dimensional morphological image and displaying a resulting image.

10. A topographic image creating method according to claim 8, wherein said step of arranging said light irradiation positions and light detection positions on said morphological image includes a step of enlarging or contracting coordinates of said light irradiation positions and light detection positions such that the reference points designated on said morphological image coincide with three-dimensional coordinate data corresponding to said reference points.

11. A topographic image creating method according to claim 8, wherein said morphological image includes a tomographic image.

12. A topographic image creating method according to claim 8, wherein said morphological image includes a CT image.

13. A topographic image creating method according to claim 8, wherein said morphological image includes a MRI image.

14. A topographic image creating method according to claim 8 further comprising a step of preparing a wire frame image of said subject as the three-dimensional morphological image of said subject.

15. A biological light measuring instrument according to claim 1, wherein said biological information comprises a change in concentration of hemoglobin.

16. A biological light measuring instrument according to claim 15, wherein said change in concentration of hemoglobin is obtained by using quantities of light detected of two wavelengths at each of said detection positions.

17. A biological light measuring instrument according to claim 16, wherein said reference points are at least three.

18. A biological light measuring instrument according to claim 16, wherein said signal processing means comprises means for performing enlargement and contraction to bring real spatial coordinate values of said reference points measured with a three-dimensional position detection device into matching with said reference points on a three-dimensional image.

19. A biological light measuring instrument according to claim 1, wherein said signal processing means comprises means for correcting a two-dimensional topographic image for distance for conversion to said three-dimensional topographic image.

20. A biological light measuring instrument according to claim 19, wherein said means for correcting a two-dimensional topographic image for distance comprises means for multiplying a signal level of said two-dimensional topographic image by a weight according to a distance.

21. A biological light measuring instrument according to claim 19, wherein said means for correcting a two-dimensional topographic image for distance uses a distance between a light irradiation position and a light detection position measured with a three-dimensional position detector.

22. A biological light measuring instrument according to claim 4, wherein said wire frame image is a three-dimensional image of a head of said subject.

23. A topographic image creating method according to claim 8, further comprising the steps of:

mounting fitting members for biological light measurement to a head of said subject applied with reference markers; and measuring real spatial coordinates of positions of reference points, light irradiation positions and light detection positions by a three-dimensional position detection device.

24. A topographic image creating method according to claim 8, further comprising the step of bringing real spatial coordinate values reference points measured with a three-dimensional position device into matching with reference points on a three-dimensional image by performing enlargement and contraction.

25. A biological light measuring system, comprising:

an image diagnostic device for obtaining a three-dimensional morphological image of a subject to be inspected;

light irradiation means for irradiating light beams from a plurality of light irradiation positions to said subject;

light detection means for detecting light beams irradiated from said plurality of light irradiation positions and passing through the inside of said subject at a plurality of detection positions arranged near said plurality of light irradiation positions;

signal processing means for preparing a topographic image representing biological information about the inside of said subject by using quantities of light detected by said light detection means at the individual detection positions;

memory means for memorizing said three-dimensional morphological image of said subject and reference points set thereon;

wherein said signal processing means includes:

means for setting three-dimensional coordinate data indicative of the positional relation between said light irradiation positions and said light detection positions and reference points set on said subject;

means for generating a three-dimensional topographic image on the basis of said three-dimensional coordinate data; and means for superimposing said three-dimensional topographic image onto said three-dimensional morphological image based on said set reference points.

* * * * *